United States Patent [19]

Hendry

[11] 4,048,618

[45] Sept. 13, 1977

[54] METHOD OF IDENTIFYING A CHECK SIGNER

[75] Inventor: Seth T. Hendry, Twin Falls, Idaho

[73] Assignee: The Raymond Lee Organization, Inc., New York, N.Y. ; a part interest

[21] Appl. No.: 744,722

[22] Filed: Nov. 24, 1976

[51] Int. Cl.² ............................................. G06K 9/00
[52] U.S. Cl. .......................... 340/146.3 E; 235/61.7 B; 340/149 A
[58] Field of Search .................... 250/221; 235/61.7 B; 340/146.3 E, 149 A, 149 R; 194/4 R, 4 F, DIG. 26

[56] References Cited

U.S. PATENT DOCUMENTS

| | | | |
|---|---|---|---|
| 3,383,657 | 5/1968 | Claassen et al. | 235/61.7 B |
| 3,412,493 | 11/1968 | French | 340/146.3 E |
| 3,584,958 | 6/1971 | Miller et al. | 340/146.3 E |
| 3,641,315 | 2/1972 | Nagata et al. | 340/149 A |
| 3,985,998 | 10/1976 | Crafton | 340/149 A |
| 3,990,558 | 11/1976 | Ehrat | 340/149 R |

*Primary Examiner*—Leo H. Boudreau
*Attorney, Agent, or Firm*—Daniel Jay Tick

[57] ABSTRACT

A method of identifying a check signer comprises the application of a fingerprint of a person to an identification card in invisible ink. The same fingerprint of the person is applied to the check in invisible ink in the presence of a person requested to cash the check. The fingerprint of the identification card is scanned to provide a first set of electrical signals. The fingerprint of the check is scanned to provide a second set of electrical signals. The first and second sets of electrical signals are compared. Comparison or non-comparison of the first and second sets of electrical signals is indicated to indicate the authenticity of the signer.

1 Claim, 6 Drawing Figures

FIG. 6

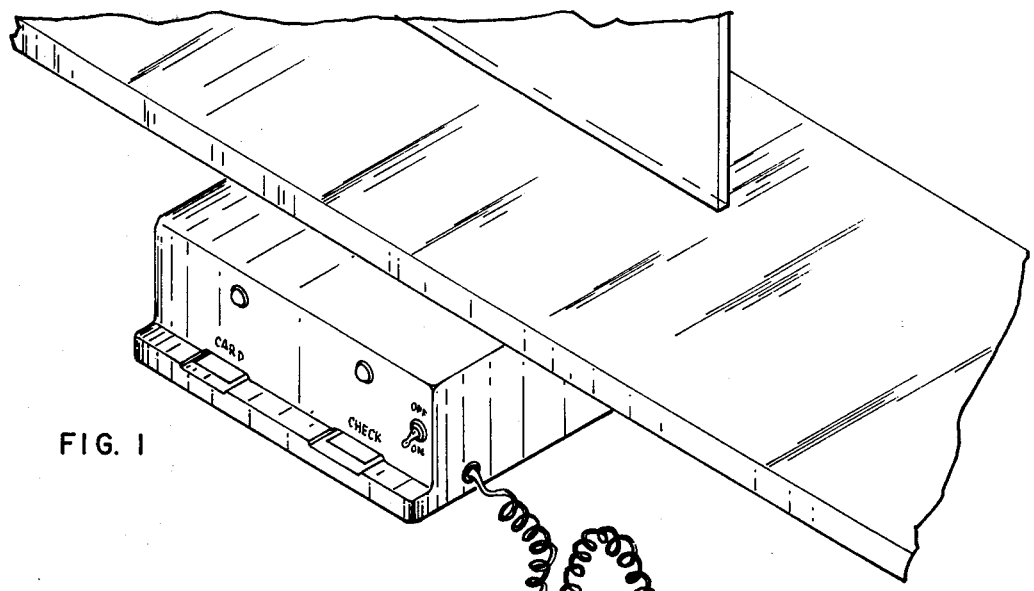
FIG. 1
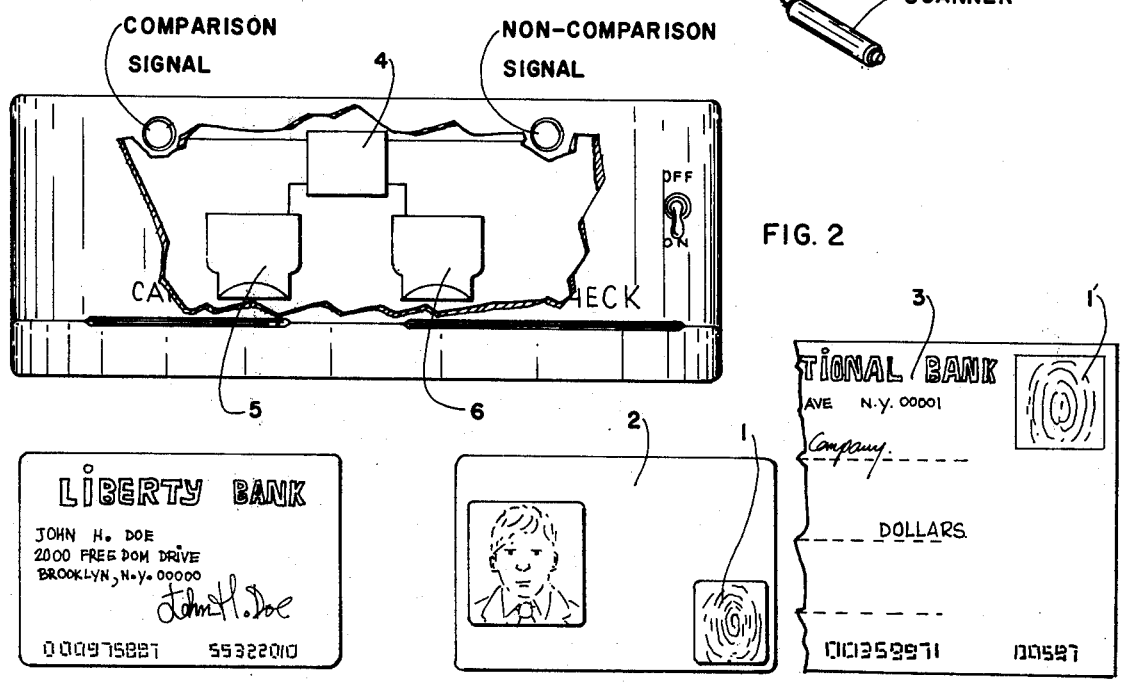
FIG. 2
FIG. 3
FIG. 4
FIG. 5
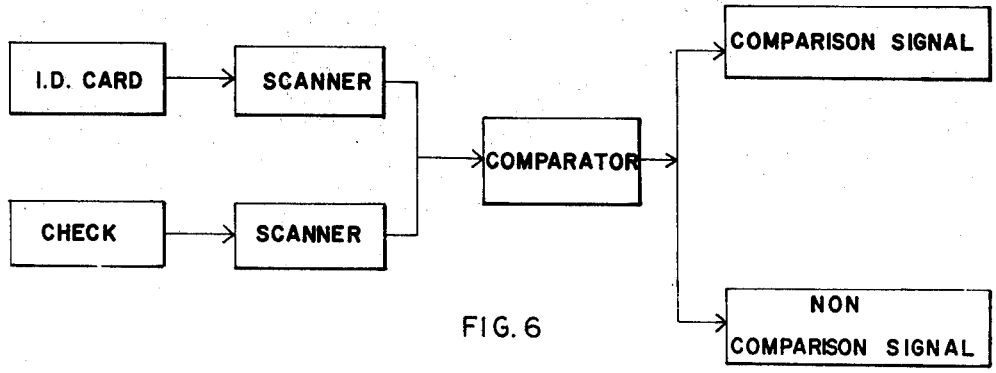
FIG. 6

METHOD OF IDENTIFYING A CHECK SIGNER

BACKGROUND OF THE INVENTION:

The present invention relates to a method of identifying a check signer.

Objects of the invention are to provide a method of identifying a check signer, which method presents an absolutely foolproof determination of the authenticity or lack of authenticity of the signer of the check to a person requested to cash the check.

BRIEF DESCRIPTION OF THE DRAWINGS:

In order that the invention may be readily carried into effect, it will now be described with reference to the accompanying drawings, wherein:

FIG. 1 is a perspective view of an embodiment of the apparatus for providing the method of the invention;

FIG. 2 is a cutaway view, on an enlarged scale, of the apparatus of FIG. 1;

FIG. 3 is a view of one side of an identification card utilized in the method of the invention;

FIG. 4 is a view of the opposite side of an identification card utilized in the method of the invention;

FIG. 5 is a view of part of a check attempted to be cashed by the method of the invention; and FIG. 6 is a block diagram of an embodiment of the apparatus for providing the method of the invention.

DETAILED DESCRIPTION OF THE INVENTION

The method of the invention identifies a check signer as authentic or non-authentic. The method of the invention involves the application of a fingerprint 1 of a person to an identification card 2 in invisible ink (FIG. 4).

The same fingerprint 1' of the person is then applied to a check 3 (FIG. 5) in invisible ink in the presence of a person requested to cash the check.

In the method of the invention the fingerprint 1 of the identification card 2 is scanned by any suitable scanning device to provide a first set of electrical signals. The fingerprint 1' of the check 3 is scanned by any suitable scanning device to provide a second set of electrical signals.

The first and second sets of electrical signals are compared in a comparator 4 of any suitable type having inputs connected to the outputs of the card scanner 5 and the check scanner 6, as shown in FIG. 6. The comparator 4 provides either a comparison signal, which indicates a comparison between the first and second sets of electrical signals and thereby the authenticity of the signer of the check, or a non-comparison signal, which indicates non-comparison of the first and second sets of electrical signals to indicate the non-authenticity of the signer of the check.

Since the fingerprints 1 and 1' are in invisible ink, the scanners 5 and 6 are preferably infrared scanners for detecting such fingerprints.

While the invention has been described by means of a specific example and in a specific embodiment, I do not wish to be limited thereto, for obvious modifications will occur to those skilled in the art without departing from the spirit and scope of the invention.

I claim:

1. A method of identifying a check signer, comprising the steps of
    applying a fingerprint of a person to an identification card in invisible ink;
    applying the same fingerprint of the person to a check in invisible ink in the presence of a person requested to cash the check;
    scanning the fingerprint of the identification card to provide a first set of electrical signals;
    scanning the fingerprint of the check to provide a second set of electrical signals;
    comparing the first and second sets of electrical signals; and
    indicating comparison or non-comparison of the first and second sets of electrical signals to indicate the authenticity of the signer.

* * * * *